(12) United States Patent
Holmqvist et al.

(10) Patent No.: US 9,220,847 B2
(45) Date of Patent: Dec. 29, 2015

(54) MEDICAMENT DELIVERY DEVICE

(75) Inventors: Anders Holmqvist, Värmdö (SE); Helen Moore, Stowmarket (GB)

(73) Assignee: SHL Group AB, Nacka Strand (SE)

( * ) Notice: Subject to any disclaimer, the term of this patent is extended or adjusted under 35 U.S.C. 154(b) by 16 days.

(21) Appl. No.: 13/978,932

(22) PCT Filed: Jan. 11, 2012

(86) PCT No.: PCT/SE2012/050012
§ 371 (c)(1),
(2), (4) Date: Aug. 16, 2013

(87) PCT Pub. No.: WO2012/096620
PCT Pub. Date: Jul. 19, 2012

(65) Prior Publication Data
US 2013/0324934 A1  Dec. 5, 2013

Related U.S. Application Data

(60) Provisional application No. 61/431,471, filed on Jan. 11, 2011.

(30) Foreign Application Priority Data

Jan. 11, 2011  (SE) .................................... 1150012-1

(51) Int. Cl.
*A61M 5/32* (2006.01)
*A61M 5/20* (2006.01)
A61M 5/34 (2006.01)

(52) U.S. Cl.
CPC ........... *A61M 5/3202* (2013.01); *A61M 5/2033* (2013.01); *A61M 5/3272* (2013.01);
(Continued)

(58) Field of Classification Search
CPC ............ A61M 5/2033; A61M 5/3272; A61M 2005/2033; A61M 2005/2013; A61M 2005/206; A61M 5/3202; A61M 5/34; A61M 2005/208; A61M 2005/3247; A61M 2005/3267

USPC .................................. 604/135, 137, 192, 198
See application file for complete search history.

(56) References Cited

U.S. PATENT DOCUMENTS 6,575,939 B1 * 6/2003 Brunel .......................... 604/187
2005/0101919 A1  5/2005 Brunnberg
(Continued)

FOREIGN PATENT DOCUMENTS

EP        0666084 A2   8/1995
GB        2461078 A    12/2009

OTHER PUBLICATIONS

Sweden Patent Office, In'tl Search Report in PCT/SE2012/050012, May 7, 2012.

(Continued)

*Primary Examiner* — Theodore Stigell
*Assistant Examiner* — Amber Stiles
(74) *Attorney, Agent, or Firm* — Piedmont Intellectual Property

(57) ABSTRACT

The present invention relates to a medicament delivery device comprising a generally elongated housing (10; 100, 102), a drive assembly disposed in said hosing and an actuation assembly operably connected to said drive assembly, wherein said drive assembly comprises a guard member (12; 104) and an actuator member (44; 180), characterized in that the actuation assembly further comprises a locking member (28; 32) disposed between the guard member and the actuator member, wherein said locking member is configured to be moved by the guard member when the guard member is pressed against a delivery site between a first locking position in which the locking member is blocking the actuator member and a released position in which the locking member allows the actuator member to be operated.

14 Claims, 13 Drawing Sheets

(52) U.S. Cl.
CPC ........... *A61M 5/34* (2013.01); *A61M 2005/208* (2013.01); *A61M 2005/3247* (2013.01); *A61M 2005/3267* (2013.01)

(56) References Cited

U.S. PATENT DOCUMENTS

| 2008/0262436 | A1* | 10/2008 | Olson | 604/198 |
| 2009/0270804 | A1* | 10/2009 | Mesa et al. | 604/111 |
| 2010/0262083 | A1* | 10/2010 | Grunhut et al. | 604/198 |
| 2010/0268170 | A1* | 10/2010 | Carrel et al. | 604/198 |

OTHER PUBLICATIONS

Sweden Patent Office, Written Opinion in PCT/SE2012/050012, May 7, 2012.

* cited by examiner

MEDICAMENT DELIVERY DEVICE

TECHNICAL AREA

The present invention relates to a medicament delivery device and in particular a medicament delivery device capable of handling medicament cartridges such as to facilitate the attachment of medicament delivery members for delivering a dose of medicament.

BACKGROUND OF THE INVENTION

Many drugs for use with medicament delivery devices are contained in so called cartridges that are generally shaped as glass tubes in which a stopper is positioned. The proximal end of the cartridge is arranged with a septum or a similar resilient membrane through which a distal end of a medicament delivery member can be pushed.

The devices are thus arranged with compartments in which these medicament containers may be placed and are further arranged with neck portions provided with attachment members intended to cooperate with corresponding attachment members on the medicament delivery members.

For a number of devices the medicament delivery members constitute injection needles. The injection needles could either be arranged to an attachment member that is designed to cooperate with corresponding attachment means on medicament cartridges in order to deliver a dose of medicament at the injection site of a patient. The injection needle could also be a part of a syringe, i.e. integrated with the medicament container.

Due to the risk of being unintentionally injured by the injection needle, but also for covering the needle before use for patients that are uncomfortable with seeing the needle during e.g. penetration, different covers, caps and/or shields and guards have been devised. These are often accompanied by spring members urging them in different directions in relation to the devices as well as locking members, releasable or non-releasable, for holding and locking the covers or shields in different positions.

Regarding the use of springs acting on the shields, they are often used to urge the shields in the proximal direction in a non-locked condition prior to drug delivery. One such device is disclosed in the document WO 2006/057604 having a needle shield that is released from a retracted position by a turning action of a dose setting member at a distal end of the device. The device of WO 2006/057604 comprises a number of functions such as mixing, priming, auto-penetration and auto-injection, making it complex with a plurality of components. Further, in order to release the needle shield, components need to extend through the whole device from the dose setting member. For some applications and uses, the device need not be so complex nor contain so many functions, but could yet be intuitive and easy to use.

BRIEF DESCRIPTION OF THE INVENTION

The aim of the present invention is to provide a medicament delivery device that can contain a medicament cartridge to which a medicament delivery member can be attached and wherein a medicament delivery member guard can be easily activated.

This aim is obtained by a medicament delivery device according to the features of the independent patent claim. Preferable embodiments of the invention form the subject of the dependent patent claims.

According to a main aspect of the invention it is characterised by a medicament delivery device comprising a generally elongated housing having opposite distal and proximal ends, and adapted to store a medicament container assembly; a drive assembly disposed in said housing and configured to act on said medicament container assembly for expelling a dose of medicament; and an actuation assembly operably connected to said drive assembly for activating said drive assembly, wherein said drive assembly comprises a guard member being movable in relation to the housing and having a proximal part protruding from the proximal end of the housing, and an actuator member disposed in said housing and being operable through the housing; wherein the actuation assembly further comprises a locking member disposed between the guard member and the actuator member, wherein said locking member is configured to be moved by the guard member when the guard member is pressed against a delivery site between a first locking position in which the locking member is blocking the actuator member and a released position in which the locking member allows the actuator member to be operated and wherein said locking member is further configured to be moved by the actuator member between the released position and a second locking position in which the locking member is blocking the guard member after said guard member is removed from the delivery site.

According to another aspect of the invention the locking member is a rotator member configured to be rotated in relation to the housing by the guard member and by the actuator member.

According to a further aspect of the invention the actuation assembly further comprises a first resilient force member arranged between the rotator member and the guard member for urging said guard member towards the proximal end.

According to another aspect of the invention the container assembly comprises a syringe having a delivery member.

According to a further aspect of the invention the container assembly comprises a cartridge having a proximal end protruding in relation to the proximal part of the guard member for allowing a delivery member to be attached to the cartridge According to yet another aspect of the invention the guard member is operably connected to the housing by guide means such that when said guard member is manually turned in relation to the housing, said guard member is forced towards the proximal end of the device by the first resilient force member and thereby covering the delivery member from sight.

According to yet a further aspect of the invention the guard member is arranged to be moved in relation to the housing when said guard member is pressed against the delivery site between an extended position in which the guard member is covering the delivery member from sight and a retracted position in which the guard member is arranged within the housing such that the resilient force member is compressed and such that the delivery member is exposed to sight.

According to another aspect of the invention the compressed resilient force member is adapted to force the guard member from the retracted position to the extended position when said guard member is removed from the delivery site.

According to a further aspect of the invention said medicament delivery device is an auto-injector.

There are a number of advantages with the present invention. By the use of a locking member arranged between the guard member and the actuator member several functions may be obtained by rather few components. Also there is created a functional link between the guard member at the proximal end of the device, where the medicament delivery member is placed, and the actuator member, such that the actuator member cannot be operated, and thereby the device actuated, until the device is pressed against a delivery site.

The locking member may be designed and arranged as a rotator member that is turnable around a longitudinal axis of the device and capable of preventing or allowing movement of the components.

Especially when the rotator is arranged with guide members cooperating with guides on the guard member as well as lock and release members, the guard member could be locked in different positions such as in a retracted position when a medicament delivery member is to be attached prior to a dose delivery, or in an extended position after dose delivery for covering the medicament delivery member in order to avoid accidental needle sticks if the medicament delivery member is an injection needle.

The rotator and other interacting components could thus comprise guides, protrusions, ledges and the like that are integrated in few components and that are moved in and out of contact, both linearly and by rotation, during different operations.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

In the present application, when the term "distal part/end" is used, this refers to the part/end of the delivery device, or the parts/ends of the members thereof, which is/are located the furthest away from the medicament delivery site. Correspondingly, when the term "proximal part/end" is used, this refers to the part/end of the delivery device, or the parts/ends of the members thereof, which, is/are located closest to the medicament delivery site.

Figure 1:
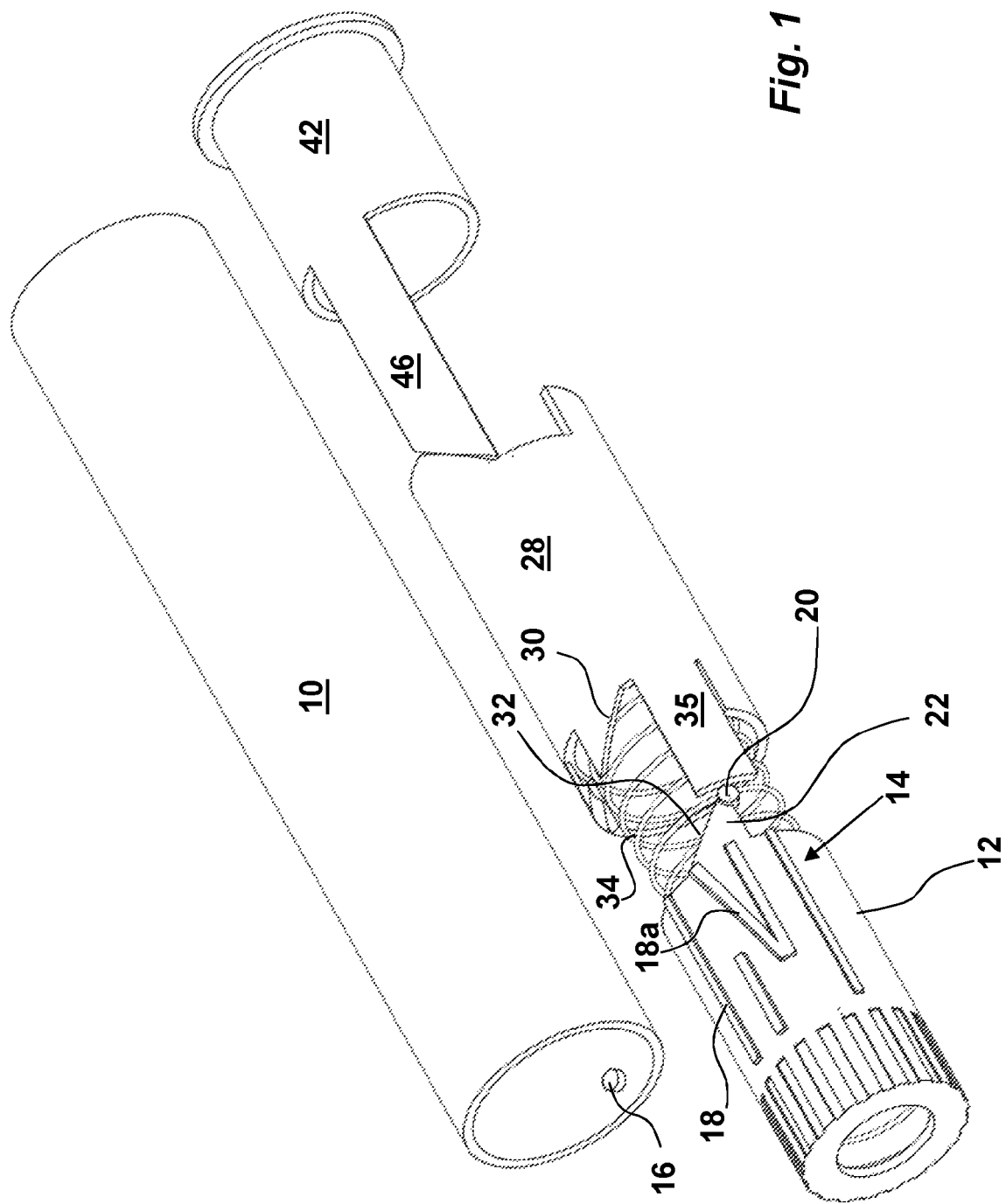
FIG. 1 is a perspective, partly exploded, view of a first embodiment of the present invention.
Figure 2:
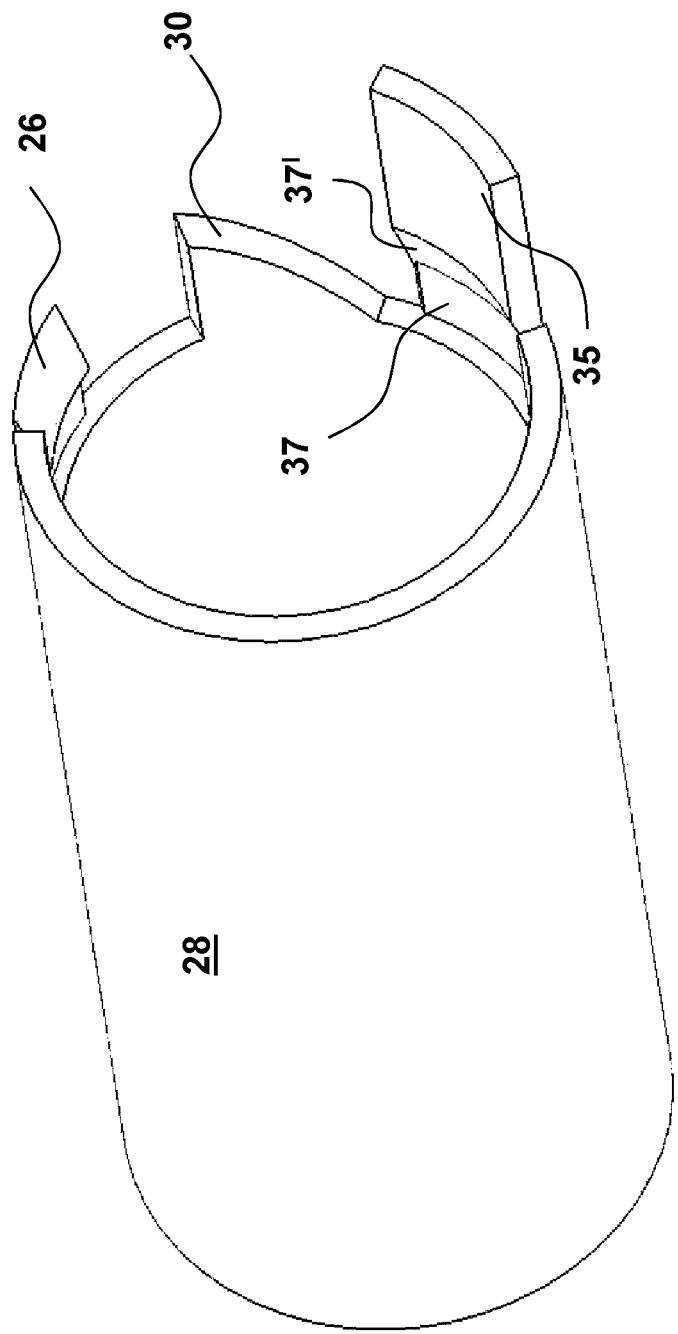
FIG. 2 is a detailed view a rotator barrel comprised in the device of FIG. 1.
Figure 3:
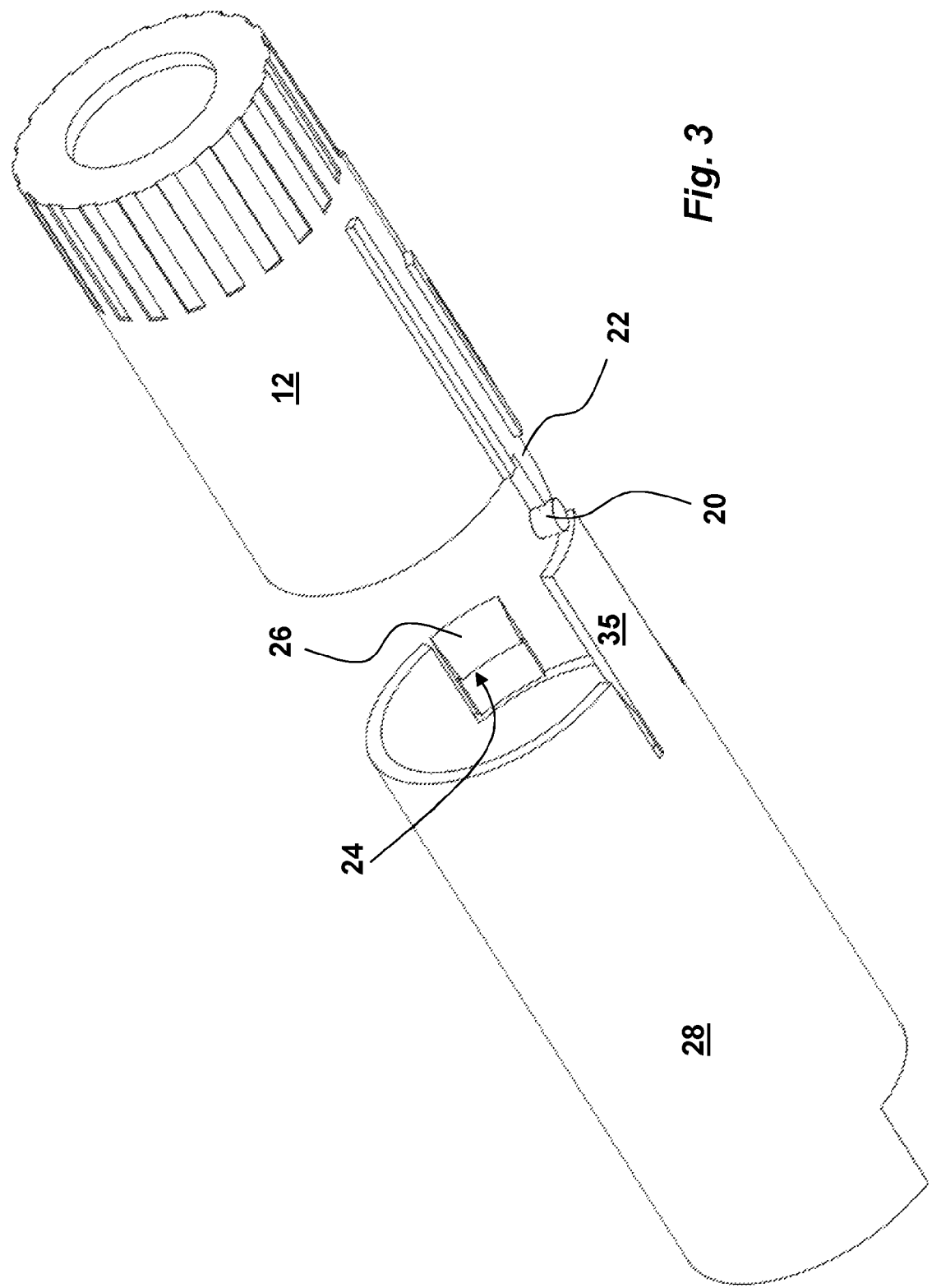
FIG. 3 is a detailed view of the rotator barrel and a medicament delivery member guard.

One exemplary embodiment of a medicament delivery according to the present invention is shown in the drawings 1-4. FIG. 1 comprises a generally tubular, elongated housing 10. At a proximal end of the housing a guard member in the form of a generally tubular needle guard 12 is arranged slidable in relation to the housing. The outer surface of the needle guard is arranged with first guide members 14. Further the inner surface of the housing at the proximal end is arranged with second guide members 16. The first and second guide members are arranged to guide the movement of the needle guard 12 as will be described below. According to the embodiment shown in FIGS. 1-4 the first guide members are in the form of ridges 18 and the second guide member are protrusions 16 that are able to glide along the ridges 18. The needle guard is further arranged with a locking member that in the embodiment shown is a protrusion 20 on an outer surface of a distally extending tongue 22. The protrusion 20 is arranged to cooperate with a locking ledge 24, FIG. 2, which locking ledge 24 is arranged on the inner surface of a proximally directed tongue 26, which tongue 26 is attached to a locking member in the form of a generally tubular rotator barrel 28, where the rotator barrel 28 is arranged rotatable inside said housing 10. The rotator barrel 28 is arranged with third guide members that in the embodiment shown are arranged as proximally directed inclined surfaces 30. The surfaces of the third guide members are cooperating with fourth guide members that in the embodiment shown are distally directed inclined surfaces 32 arranged on the tongue 22 of the needle guard. A spring member 34 is arranged between the rotator barrel 28 and the needle guard 12 for urging the latter in the proximal direction of the device. Further the rotator barrel 28 comprises a proximally directed lock tab 35. On an area 37 of the inner surface of the lock tab 35, FIG. 2, adjacent the rotator barrel 28, material has been removed. Further a sloping transition $37^I$ is provided between the surfaces of the area 37 and the rest of the inner surface of the lock tab 35, the function of which will be described below.

Figure 4:
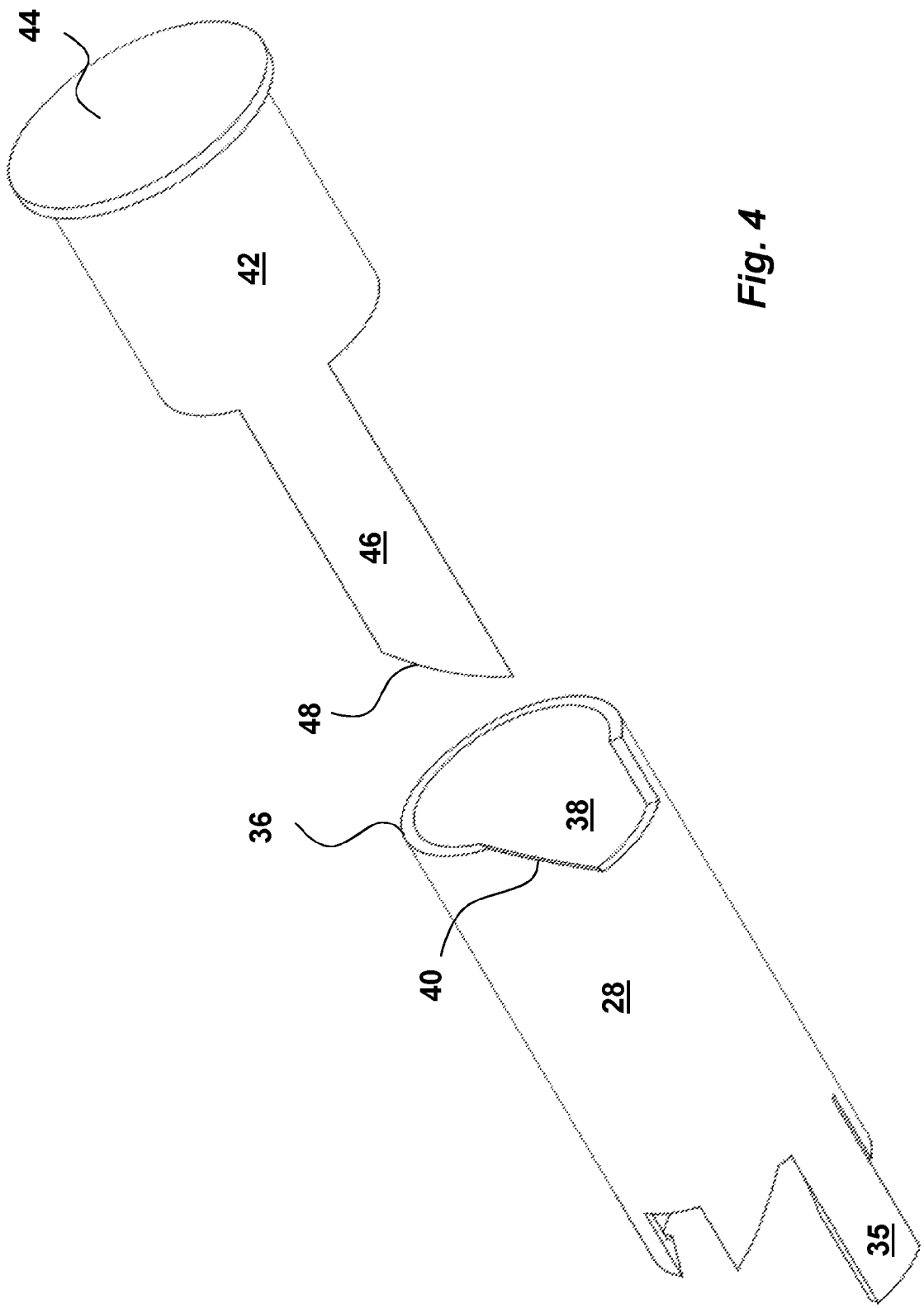
FIG. 4 is a detailed view of the rotator barrel and an actuation member.
Figure 5:
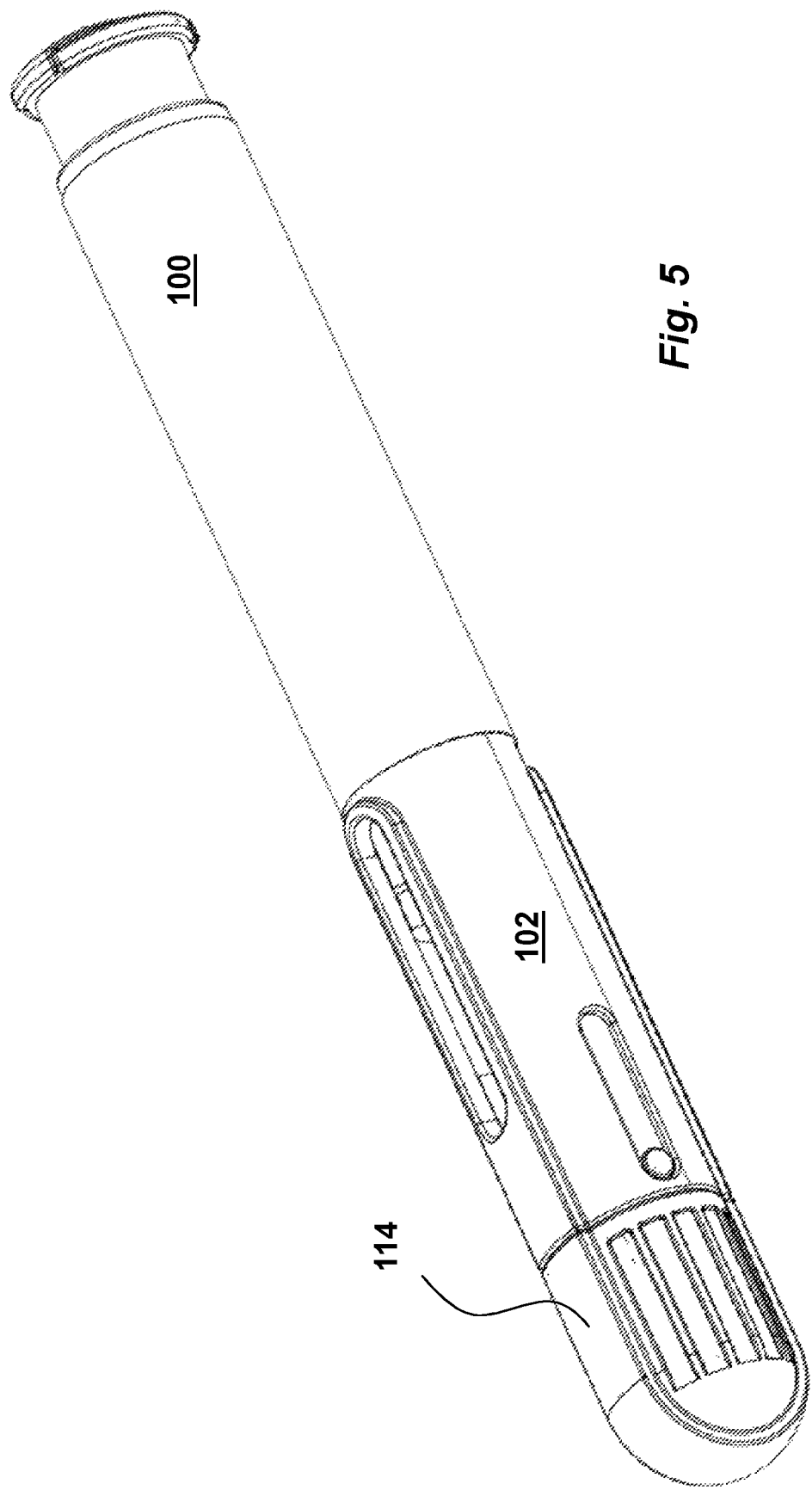
FIG. 5 is a perspective view of a second embodiment of the present invention.
Figure 6:
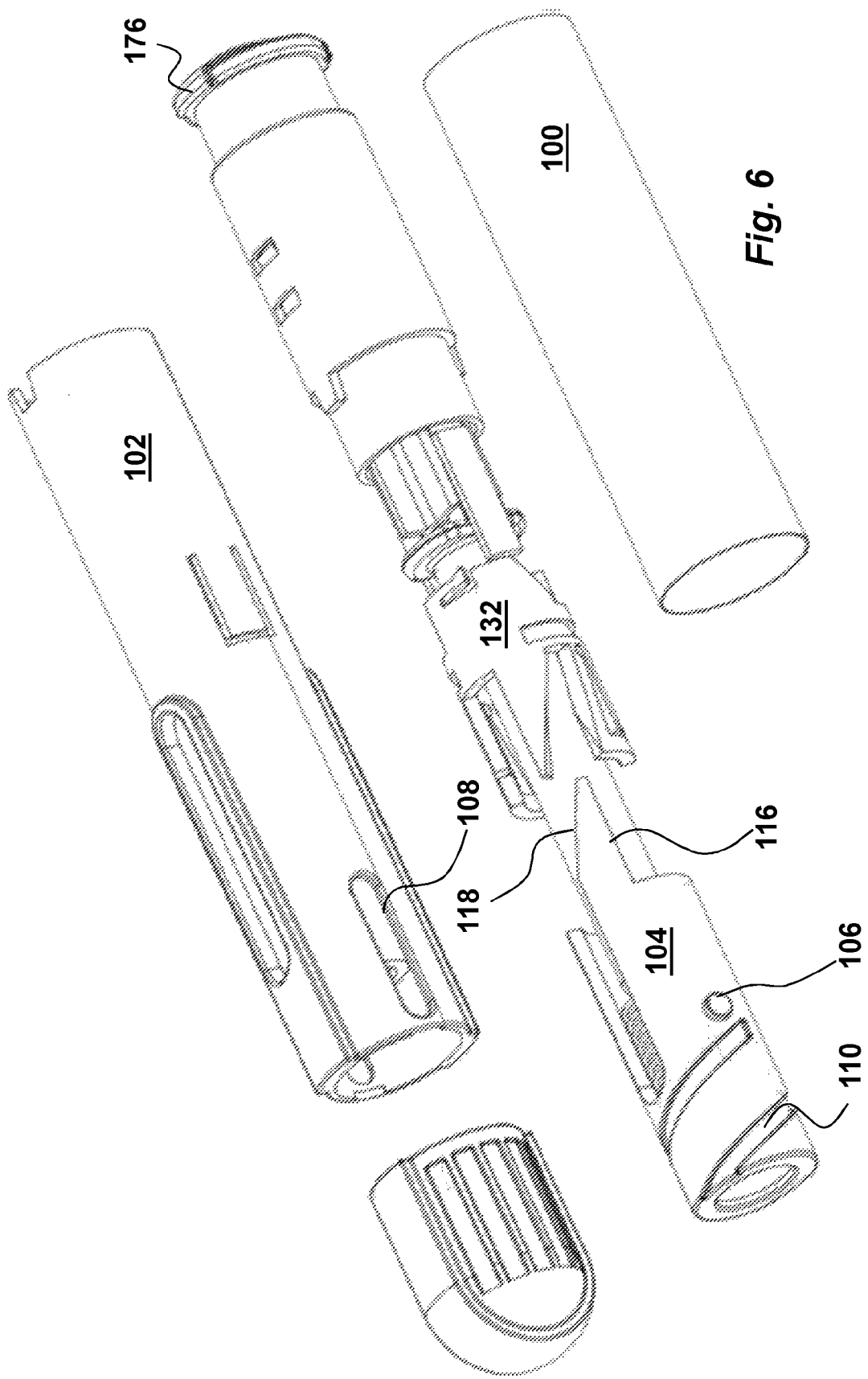
FIG. 6 is a partly exploded view of the device of FIG. 5.
Figure 7:
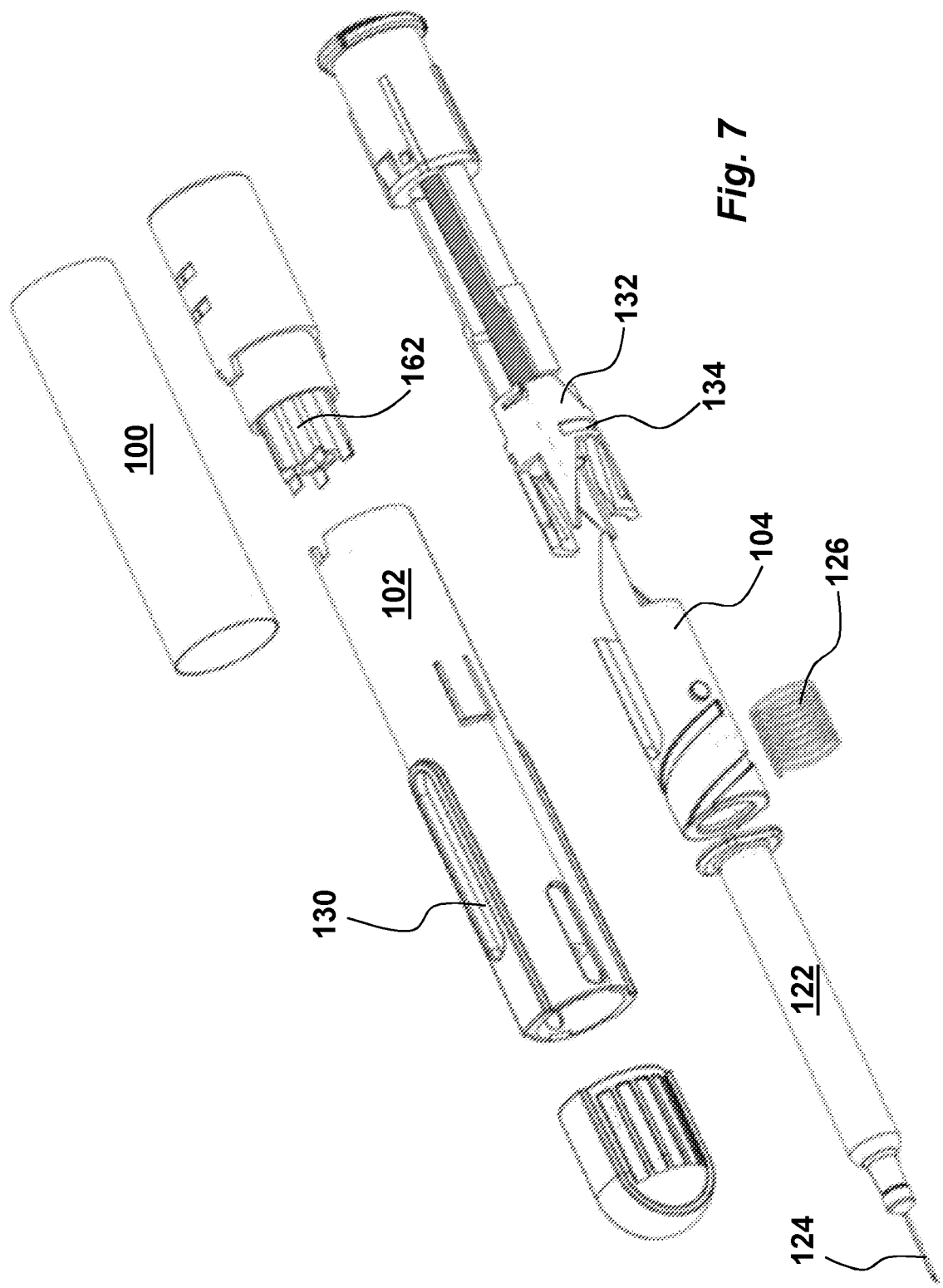
FIG. 7 is a further exploded view of the device of FIG. 5.

The distal end of the rotator barrel 28 is arranged with second locking and release member that in the embodiment shown comprises a distally directed end surface 36 of the rotator barrel and a cut-out 38, FIG. 4, which cut-out 38 is provided with an inclined side surface 40. Further an actuation member 42 is arranged in the distal end of the device that in the embodiment shown comprises an actuation member in the form of an actuation button 44 protruding through the distal end. The actuation button 44 is arranged with a proximally directed tongue 46 having an inclined proximally directed surface 48.

The device according to the first embodiment is intended to function as follows. When the device is delivered to the user, the needle guard 12 is in a retracted position inside the housing, exposing a proximal end part of a medicament cartridge (not shown). The needle guard 12 is held in the retracted position by the protrusion 20 of the needle guard 12 abutting the ledge 24 of the rotator barrel 28. Thus it is easy for a user to attach a medicament delivery member such as e.g. an injection needle, to the medicament cartridge.

In order to activate the device for delivering a dose of medicament, the user turns the needle guard 12 whereby the protrusion 20 is moved out of contact with the ledge 24. The needle guard 12 is thus free to move in the proximal direction by the force of the spring 34, thereby covering the medicament delivery member. The movement of the needle guard 12 causes the protrusion 16 on the housing 10 to move along the ridges 18 of the needle guard 12. Certain ridges 18a are somewhat inclined in relation to the longitudinal direction of the device, whereby the needle guard 12 is rotated somewhat such that the inclined surface 32 of the tongue 22 of the needle guard 12 is moved in line with the proximally directed inclined surface 30 of the rotator barrel 28. During the above operations, the actuation member 42 is locked from actuation because the proximal end of the tongue 46 is in contact with the distal end surface 36 of the rotator barrel 28.

The next step is to perform a dose delivery at a dose delivery site. The user then presses the proximal end of the needle guard 12 against the dose delivery site, causing a penetration when the medicament delivery member is an injection needle, whereby the needle guard 12 is moved in the distal direction against the force of the spring 34. This movement of the needle guard 12 causes the inclined surface 32 of the tongue 22 to move in contact and act on the inclined surface 30 of the rotator barrel 28. This action causes the rotator barrel 28 to rotate a certain distance such that the inclined side surface 40 of the cut-out 38 of the rotator barrel 28 is moved in line with the inclined end surface 48 of the tongue of the actuation member 42.

The next step is to perform a dose delivery. The user then presses the actuation button 44 in the proximal direction. This forces the plunger rod to move in the proximal direction, whereby the stopper of the medicament cartridge is also moved in the proximal direction, causing a dose of medicament to be expelled through the medicament delivery member. The movement of the actuation button 44 in the proximal direction causes the inclined surfaces 40, 48 to cooperate such that the rotator barrel 28 is rotated a certain distance. The rotation of the rotator barrel causes the protrusion 20 to come in contact with, and move onto, the area 37.

When now the device is removed from the injection site, the needle guard 12 is again free to move in the proximal direction by the spring 34, whereby the protrusion 20 of the needle guard 12 is moved from the area 37, over the transition $37^I$ and then past a proximal end surface of the lock tab 35, FIG. 1. In this position, the needle guard 12 is locked in the extended position, protecting the medicament delivery member, thereby avoiding unintentional needle sticks if the medicament delivery member is an injection needle.

FIGS. 5-13 show a second exemplary embodiment of the present invention. It comprises a generally elongated tubular distal housing part 100. The distal housing part is connected to a generally tubular proximal housing part 102. At the proximal end of the proximal housing part 102 a guard member in the form of a medicament delivery member guard 104 is arranged. The medicament delivery member guard 104 is arranged with outwardly directed protrusions 106, which protrusions 106 fit into elongated grooves 108 in the proximal housing part 102 such as to enable sliding in the longitudinal direction of the medicament delivery member guard but a rotational lock. The proximal end of the medicament delivery member guard is arranged with a helical groove 110 on its outer surface, which groove 110 is arranged to cooperate with a helically extending ridge 112 on an inner surface of a protection cap 114. The distal end of the medicament delivery member guard is arranged with two distally directed tongues 116, where each tongue is arranged with an inclined distally directed surface 118.

The proximal housing part 102 is further arranged with a medicament container holder 120, in the embodiment shown integrated with the proximal housing part 102. The medicament container holder is adapted to receive a medicament container 122, in the embodiment shown a syringe provided with a medicament delivery member 124 in the form of an injection needle. It is however to be understood that other types of medicament delivery members such as mouth or nose pieces, nozzles, nebulisers and the like can be utilized. A compression spring 126 is arranged between a proximal end surface 128, FIG. 8, of the medicament container holder 120 and a distally directed surface inside the medicament delivery member guard 104. Further both the medicament container holder and the proximal housing part are arranged with openings or windows 130 such that the medicament container 122 is visible, and since preferably the medicament container 122 is made of a transparent material, the content of the medicament container 122 is visible to a user.

Figure 11:
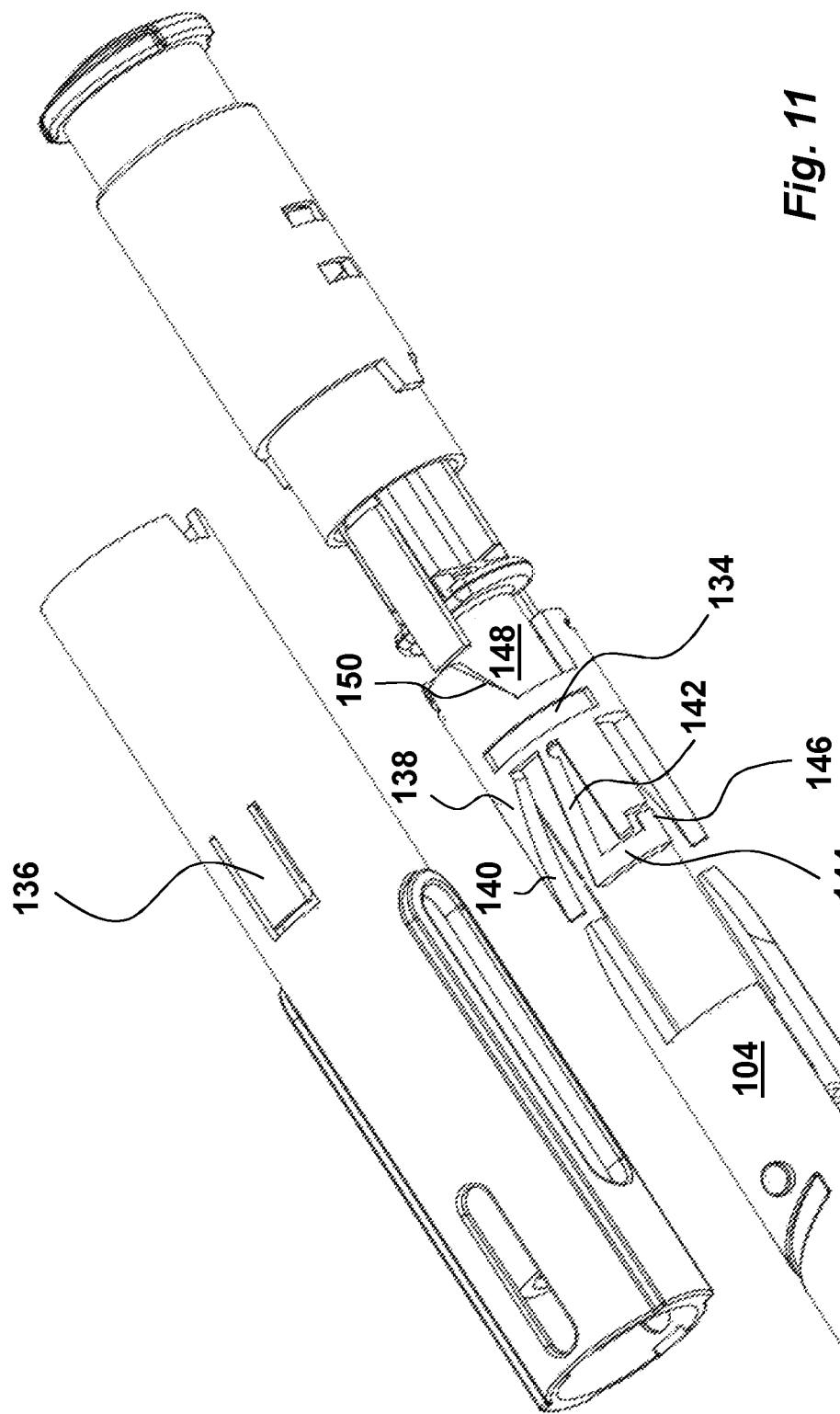
FIG. 11 is another partly exploded view of the device of FIG. 5.
Figure 12:
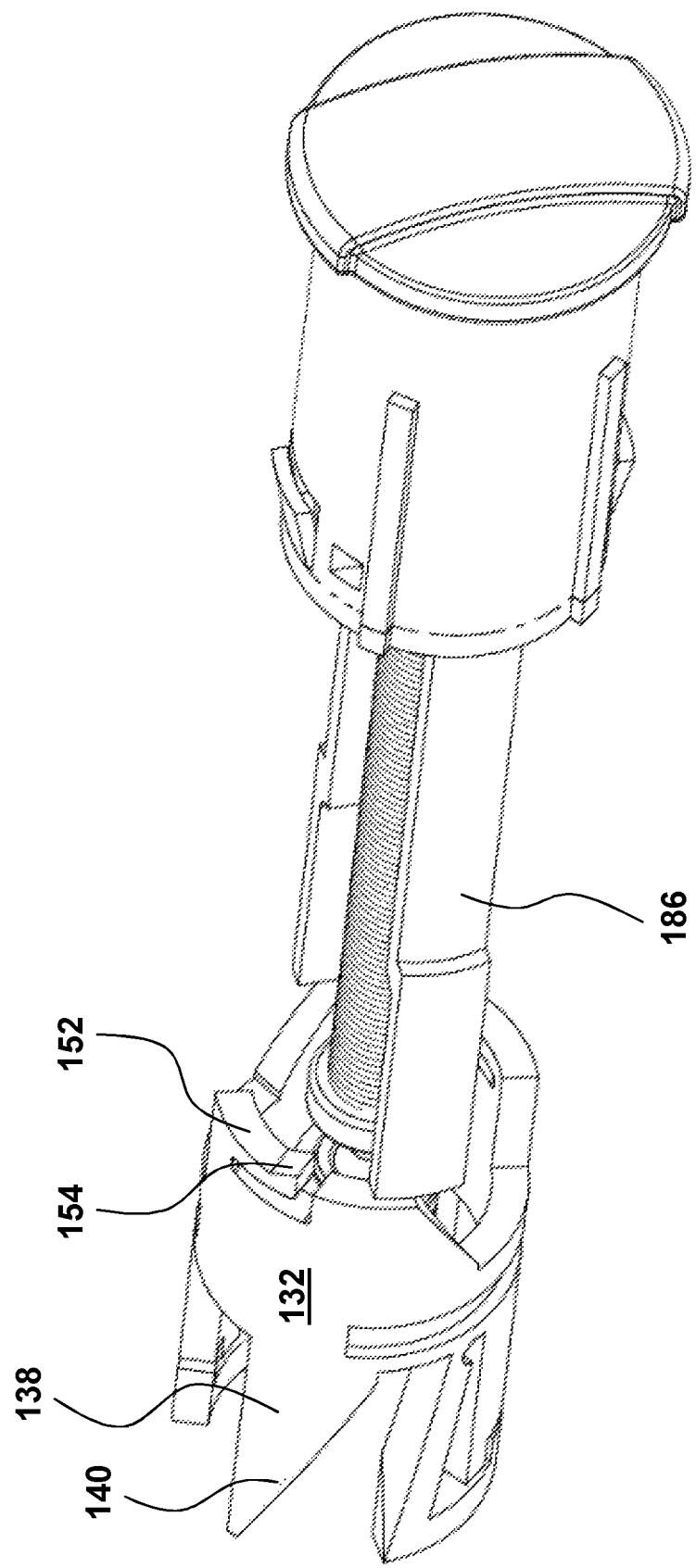
FIG. 12 is a detailed view of a rotator member and an actuation mechanism comprised in the device of FIG. 5.
Figure 13:
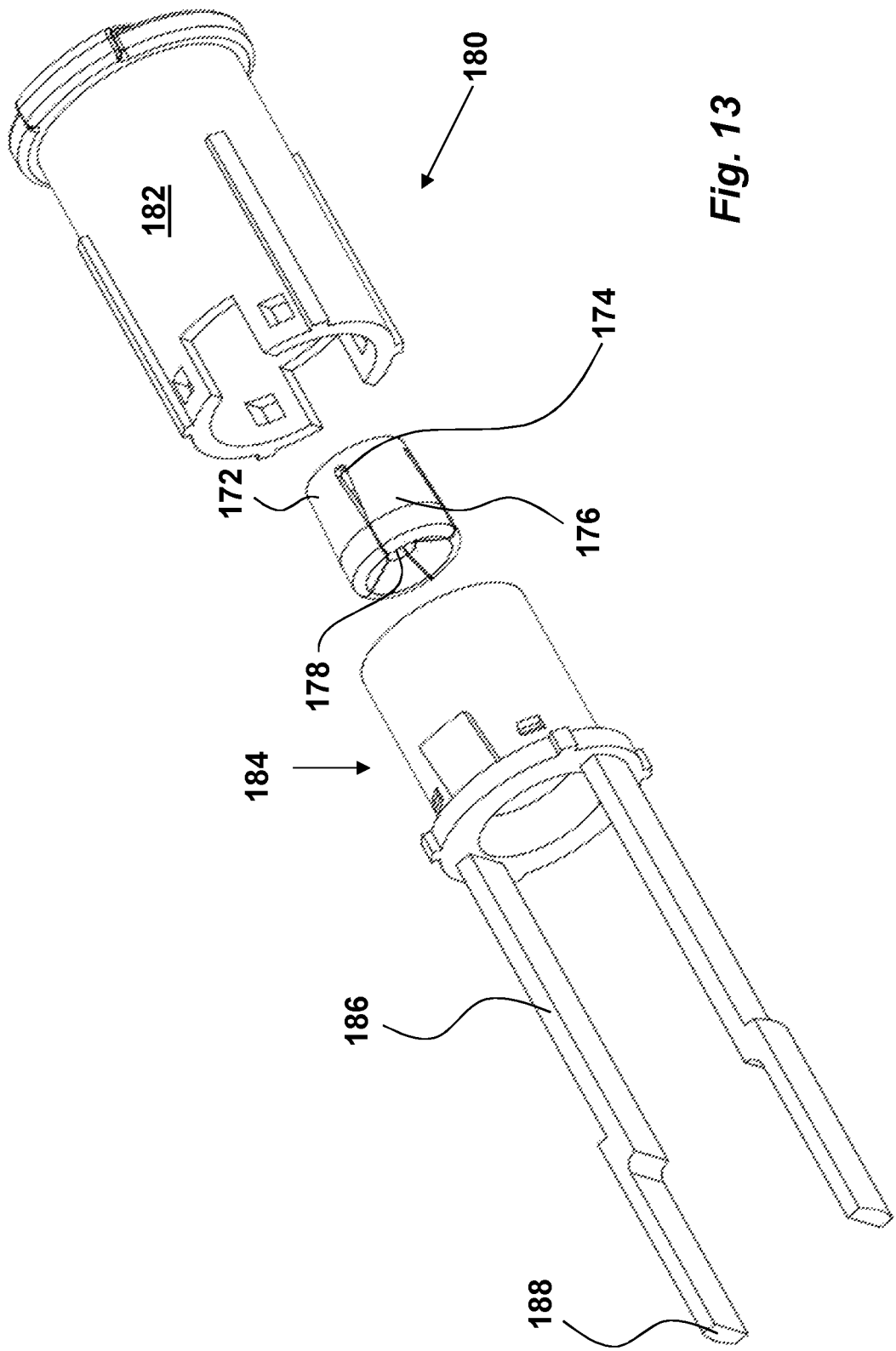
FIG. 13 is an exploded detailed view of an actuation mechanism, comprised in the device of FIG. 5.

Surrounding the medicament container holder 120 is a locking member in the form of a rotator barrel 132 arranged rotatably but locked against linear movement due to circumferentially extending grooves 134 on the outer surface of the rotator barrel cooperating with inwardly extending protrusions on flexible arms 136 arranged to the proximal housing part, FIG. 11. The rotator barrel is further arranged with proximally directed tongues 138, FIG. 11, which tongues 138 are arranged with inclined surfaces 140 intended to cooperate with the inclined surfaces 118 of the tongues of the needle guard. A flexible proximally extending arm 142 is further attached to the proximal end surface of the rotator barrel, having an inclined direction generally corresponding to the inclined surface 140 of the tongue 138. At the proximal end of the flexible arm 142 a circumferentially extending arm portion 144 is attached. At the end of the arm portion 144 a distally directed ledge 146 is attached or made integral, which distal ledge 146 is positioned in a cut out of the rotator barrel 132, FIG. 11. The distal end of the rotator barrel 132 is provided with cut-outs 148, where each cut-out 148 is arranged with an inclined side surface 150. Further the distally directed end surface of the rotator barrel is arranged with circumferentially extending flexible arms 152, FIG. 12, which arms 152 are arranged with distally directed wedge-shaped protrusions 154. The protrusions 154 are intended to cooperate with a corresponding wedge-shaped ratchet 156, FIG. 10, on a proximal wall surface inside the proximal housing part 102.

Figure 8:
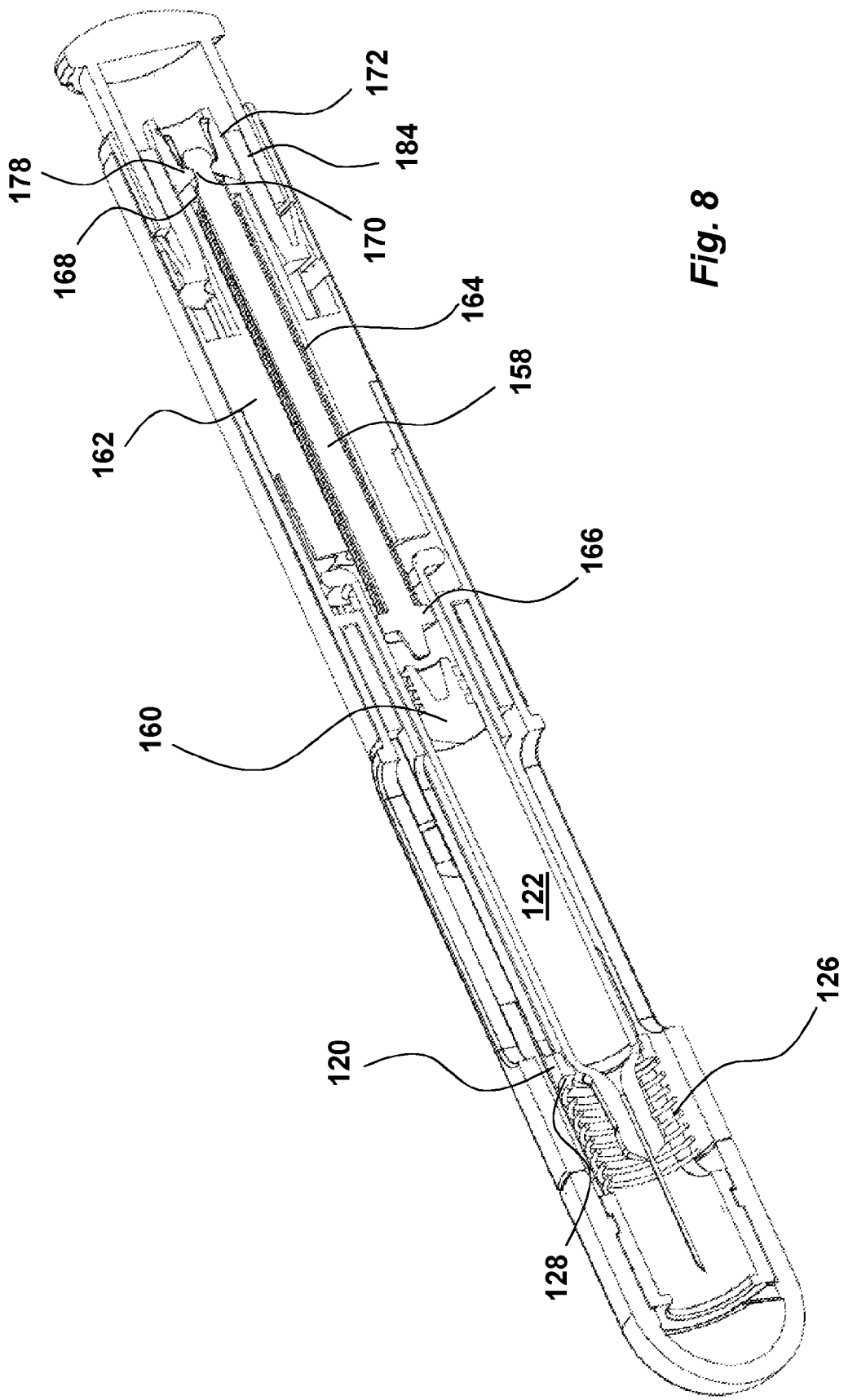
FIG. 8 is a cross-sectional view of the device of FIG. 5.
Figure 9:
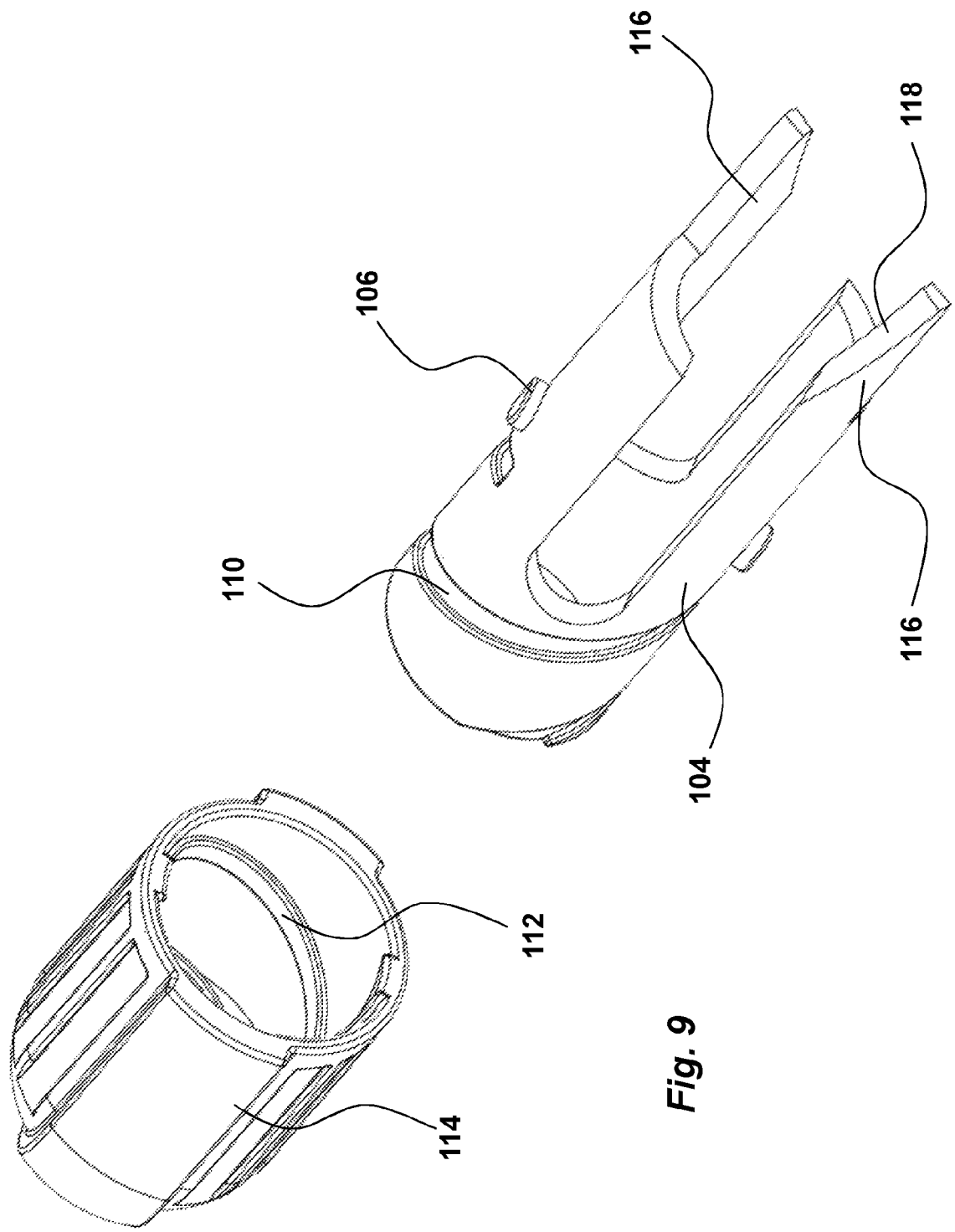
FIG. 9 is a detailed view of a rotator member comprised in the device of FIG. 5.
Figure 10:
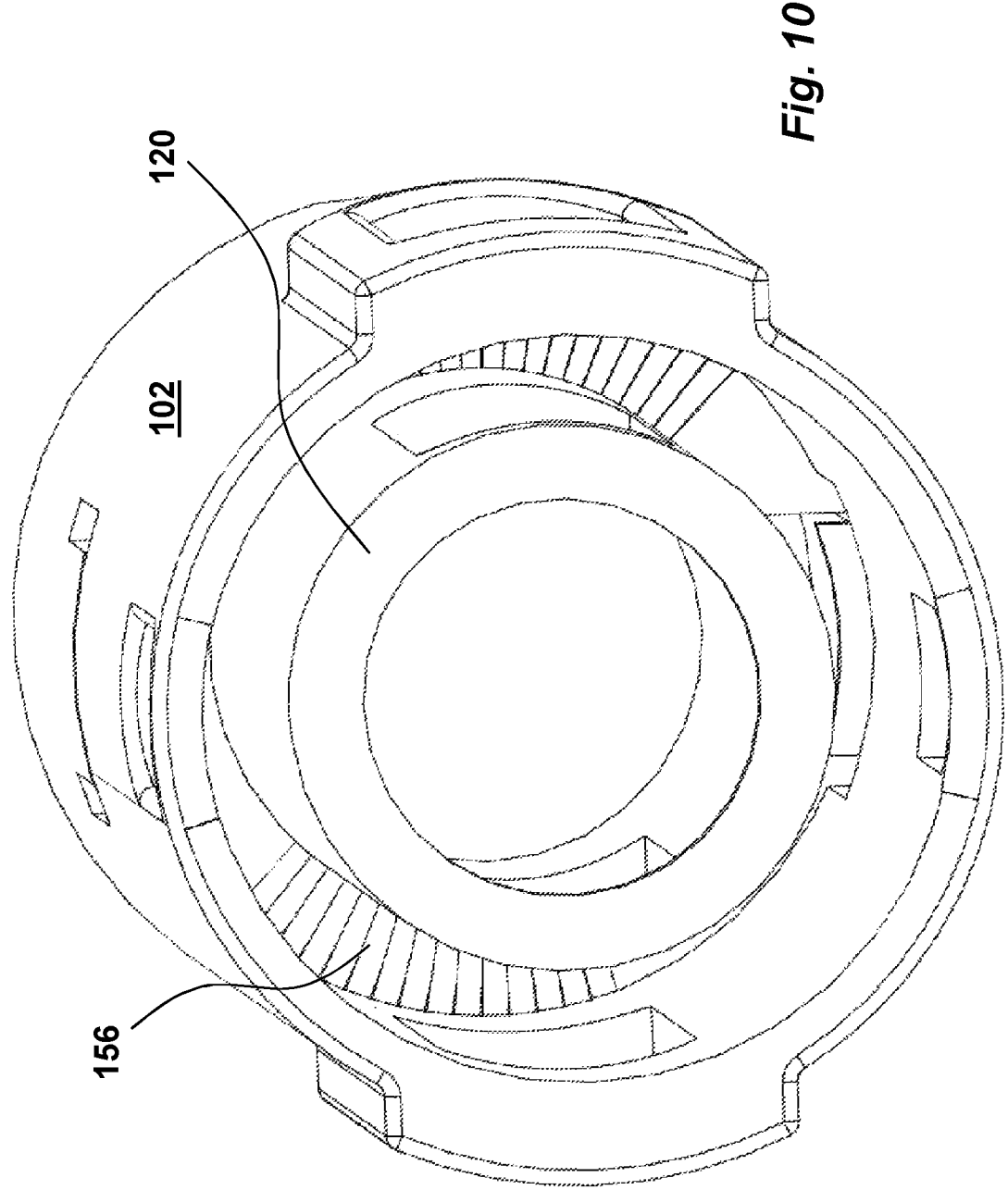
FIG. 10 is a detailed view of a medicament container holder comprised in the device of FIG. 5.

Further an elongated plunger rod 158, FIG. 8, is arranged inside the housing of the device, having a proximal end in contact with a movable stopper 160 arranged inside the medicament container 122. The plunger rod extends inside a tubular compartment of a guide member 162 positioned in the distal housing part 100. A drive spring 164 in the form of a coiled compression spring is arranged surrounding the plunger rod with its proximal end in contact with a circumferential ledge 166 attached to the proximal end of the plunger rod and with its distal end in contact with an end wall 168 of the guide member 162, FIG. 8. The distal end is further extending through a central passage of the end wall 168 of the guide member 162. The distal end of the plunger rod is further provided with a circumferential ledge 170. A locking means 172 is surrounding the distal end of the plunger rod. The locking means comprises a generally tubular shape having a number of slits 174, thereby forming flexible arms 176. The ends of the arms are provided with inwardly directed protrusions 178, which cooperate with the circumferential ledge 170 of the plunger rod 158 for locking it in place. A proximal end surface of the locking means 172 is abutting a distal end surface of the guide member 162.

Further an actuator member 180 is arranged at the distal end of the device. It comprises an actuation button 182 protruding through the distal end of the device. The proximal end of the actuation button 182 is designed generally tubular. The actuation button of the actuation member is attached to a lock/release member 184, having a generally tubular shape. The lock/release member 184 is surrounding, and in contact with, the locking member 172, preventing its flexible arms 176 from flexing radially outwardly. The lock/release member 184 is further arranged with proximally extending arms 186, having proximal end surfaces 188 adjacent the distal end surface of the rotator barrel, FIG. 13.

The device is intended to function as follows. The device preferably is delivered with a medicament container 122 mounted inside. When a dose is to be delivered the protective cap 114 is removed. The medicament delivery member guard 104 is urged in the proximal direction by the spring 126, thereby covering the medicament delivery member. The actuation button 182 can not be pressed because the proximal end surfaces 188 of the arms 186 come in contact with the distal end surfaces of the rotator barrel 132, preventing any movement of the actuation member 180.

The patient then places the proximal end of the device against a dose delivery site, such as e.g. an injection site. The medicament delivery member guard 104 is then pushed in the distal direction, exposing the medicament delivery member 124. The medicament delivery member guard 104 can only move linearly due to the protrusions 106 sliding in the grooves 108. The distal movement of the medicament delivery member guard 104 causes its inclined surfaces 118 to come in contact with the inclined surfaces 140 of the rotator barrel 132, causing a rotation of the rotator barrel 132. When the medicament delivery member guard 104 has been pushed a certain distance distally, for example corresponding to a penetration depth if the medicament delivery member 124 is an injection needle, the rotator barrel 132 has rotated such that the cut-outs 148 of the distal end of the rotator barrel 132 are in line with the arms 186 of the lock/release member 184.

When now the patient pushes the actuation button 182 in the proximal direction the lock/release member 184 is also moved in the proximal direction and in relation to the stationary locking member 172 until the distal end surface of the lock/release member 184 passes a proximal end surface of the locking means 172. Then the arms 176 of the locking means 172 are free to flex outwardly in the radial direction, thereby releasing the plunger rod 158. The plunger rod 158 is now forced in the proximal direction by the drive spring 164, whereby the plunger rod 158 pushes the stopper 160 in the proximal direction and a dose of medicament is delivered through the medicament delivery member 124.

The pushing of the actuation button 182 also causes the arms 186 to act on the inclined side surfaces 150 of the cut-outs 148 of the rotator barrel 132 so that the latter is rotated a further distance. The rotation of the rotator barrel 132 causes the flexible arms 142 to move in contact with a side surface of the distally directed tongues 116 of the needle guard 104 and to flex in the circumferential direction. The flexible arms 152 on the distal end of the rotator barrel 132 cooperate with the ratchet 156 of the housing to prevent any return movement of the rotator barrel 132.

After the dose delivery the device is removed from the dose delivery site whereby the medicament delivery member guard 104 is pushed in the proximal direction by the action of the spring 126. The proximal movement of the medicament delivery member guard 104 causes its distally directed tongues 116 to move out of contact with the flexible arms 142, whereby the latter are free to move in the circumferential direction such that their proximal end surfaces are in line with the distal end surfaces of the tongues 116 of the needle guard 104. Thereby the needle guard 104 is prevented from being pushed in the distal direction, whereby the needle guard surrounds and protects the medicament delivery member, which, in the case of an injection needle, prevents any unintentional needle sticks on a used and contaminated injection needle. The device can now be discarded.

It is to be understood that the embodiments described above and shown in the drawings are to be regarded as only exemplary embodiments of the invention and that it may be modified in many ways within the scope of the patent claims.

The invention claimed is:

1. A medicament delivery device, comprising:
    an elongated housing having opposite distal and proximal ends and configured for storing a medicament container assembly;
    a drive assembly disposed in the housing and configured for acting on the medicament container assembly to expel a dose of medicament; and
    an actuation assembly operably connected to the drive assembly for activating the drive assembly;
    wherein the drive assembly comprises a guard member movable in relation to the housing and having a proximal part protruding from the proximal end of the housing, and an actuator member disposed in the housing and operable through the housing; the actuation assembly comprises a locking member that is disposed between the guard member and the actuator member and that is configured to be moved by the guard member when the guard member is pressed against a delivery site between a first locking position, in which the locking member blocks the actuator member, and a released position, in which the locking member allows the actuator member to be operated; and the locking member is further configured to be directly moved by the actuator member between the released position and a second locking position, in which the locking member blocks the guard member after the guard member is removed from the delivery site, the guard member returning to its initial position if the locking member is not in the second locking position.

2. The medicament delivery device of claim 1, wherein the locking member includes a rotator member configured to be rotated in relation to the housing by the guard member and by the actuator member.

3. The medicament delivery device of claim 2, wherein the actuation assembly further comprises a first resilient force member arranged between the rotator member and the guard member for urging the guard member toward the proximal end.

4. The medicament delivery device of claim 3, wherein the medicament container assembly comprises a syringe having a delivery member.

5. The medicament delivery device of claim 3, wherein the medicament container assembly comprises a cartridge having a proximal end protruding in relation to the proximal part of the guard member for allowing a delivery member to be attached to the cartridge.

6. The medicament delivery device of claim 5, wherein the guard member is arranged to be moved in relation to the housing when the guard member is pressed against the delivery site between an extended position, in which the guard member covers the delivery member from sight, and a retracted position, in which the guard member is arranged within the housing such that the first resilient force member is compressed and such that the delivery member is exposed to sight.

7. The medicament delivery device of claim 6, wherein compression of the first resilient force member forces the guard member from the retracted position to the extended position when the guard member is removed from the delivery site.

8. The medicament delivery device of claim 5, wherein the guard member is operably connected to the housing by a guide such that when the guard member is manually turned in relation to the housing, the guard member is forced toward the proximal end of the medicament delivery device by the first resilient force member, thereby covering the delivery member from sight.

9. The medicament delivery device of claim 8, wherein the guard member is arranged to be moved in relation to the housing when the guard member is pressed against the delivery site between an extended position, in which the guard member covers the delivery member from sight, and a retracted position, in which the guard member is arranged within the housing such that the first resilient force member is compressed and such that the delivery member is exposed to sight.

10. The medicament delivery device of claim 9, wherein compression of the first resilient force member forces the guard member from the retracted position to the extended position when the guard member is removed from the delivery site.

11. The medicament delivery device of claim 1, wherein the medicament delivery device is an auto-injector.

12. The medicament delivery device of claim 1, wherein the actuation member includes an actuation push button.

13. The medicament delivery device of claim 1, wherein the actuator member is manually operable directly through the housing.

14. The medicament delivery device of claim 1, wherein the actuator member protrudes distally from the housing.

* * * * *